(12) United States Patent
Beilfuss et al.

(10) Patent No.: US 10,519,144 B2
(45) Date of Patent: Dec. 31, 2019

(54) CONDENSATION PRODUCT OF 1-AMINO-2-PROPANOL AND FORMALDEHYDE AND THE USE THEREOF FOR REDUCING THE AMOUNT OF HYDROGEN SULPHIDE IN LIQUIDS AND GASES

(71) Applicant: Schulke & Mayr GmbH, Norderstedt (DE)

(72) Inventors: Wolfgang Beilfuss, Hamburg (DE); Ralf Gradtke, Tornesch (DE); Jennifer Knopf, Hamburg (DE); Klaus Weber, Hamburg (DE)

(73) Assignee: VINK CHEMICALS GMBH & CO. KG, Kakenstorf (DE)

( * ) Notice: Subject to any disclaimer, the term of this patent is extended or adjusted under 35 U.S.C. 154(b) by 0 days.

(21) Appl. No.: 15/657,587

(22) Filed: Jul. 24, 2017

(65) Prior Publication Data

US 2018/0030041 A1    Feb. 1, 2018

(30) Foreign Application Priority Data

Jul. 28, 2016    (DE) .................. 10 2016 113 930

(51) Int. Cl.

| C07D 413/04 | (2006.01) |
|---|---|
| C07C 215/08 | (2006.01) |
| C07C 47/04 | (2006.01) |
| B01D 53/14 | (2006.01) |
| C07D 233/02 | (2006.01) |
| B01D 53/48 | (2006.01) |
| C08G 12/06 | (2006.01) |
| B01D 53/78 | (2006.01) |

(52) U.S. Cl.
CPC ....... *C07D 413/04* (2013.01); *B01D 53/1468* (2013.01); *B01D 53/48* (2013.01); *B01D 53/78* (2013.01); *C07C 47/04* (2013.01); *C07C 215/08* (2013.01); *C07D 233/02* (2013.01); *C08G 12/06* (2013.01); *B01D 2252/20484* (2013.01); *B01D 2252/502* (2013.01); *B01D 2257/304* (2013.01); *B01D 2257/306* (2013.01)

(58) Field of Classification Search
CPC .... C07D 413/04; C07D 233/02; C07C 47/04; C07C 215/08; B01D 53/1468; B01D 53/48; B01D 53/78; B01D 2252/20484; B01D 2252/502; B01D 2257/304; B01D 2257/306; C08G 12/06
USPC ........................................................ 548/220
See application file for complete search history.

(56) References Cited

U.S. PATENT DOCUMENTS

| 4,148,905 | A | 4/1979 | Eggensperger et al. |
|---|---|---|---|
| 4,166,122 | A | 8/1979 | Paulus et al. |
| 6,355,679 | B1 | 3/2002 | Beilfuss et al. |
| 8,329,063 | B2 | 12/2012 | Beilfuss et al. |
| 8,512,449 | B1 | 8/2013 | Zaid et al. |
| 8,568,754 | B2 | 10/2013 | Beilfuss et al. |
| 2003/0234383 | A1 | 12/2003 | Titley et al. |
| 2015/0041411 | A1 | 2/2015 | Gradtke et al. |

FOREIGN PATENT DOCUMENTS

| DE | 26 35 389 A1 | 2/1978 |
|---|---|---|
| DE | 27 11 106 A1 | 9/1978 |
| DE | 229 707 A1 | 11/1985 |
| DE | 197 22 858 A1 | 11/1998 |
| DE | 102 44 442 A1 | 4/2004 |
| DE | 10 2004 014 447 A1 | 10/2005 |
| DE | 10 2012 203 003 A1 | 8/2013 |
| EP | 0 347 815 A2 | 12/1989 |
| WO | 90/07467 A1 | 7/1990 |
| WO | 94/08980 A1 | 4/1994 |
| WO | 96/05907 A1 | 2/1996 |
| WO | 97/25126 A1 | 7/1997 |
| WO | 98/02501 A1 | 1/1998 |
| WO | 02/051968 A1 | 7/2002 |
| WO | 2013/101361 A1 | 7/2013 |
| WO | 2016/105341 A1 | 6/2016 |

OTHER PUBLICATIONS

DE Office Action, dated Apr. 13, 2017, from corresponding DE 102016113930.3 application.

*Primary Examiner* — Kristin A Vajda
(74) *Attorney, Agent, or Firm* — Young & Thompson

(57) ABSTRACT

Disclosed is a storage-stable condensation product prepared from 1-amino-2-propanol and formaldehyde in a molar ratio in the range from 1:2.0 to 1:3.1. The condensation product contains less than 10% by weight of water. Also, disclosed is the preparation of the condensation product and the use thereof for reducing the amount of hydrogen sulphide in liquids and gases.

19 Claims, 1 Drawing Sheet

Analytical system for the determination of H₂S
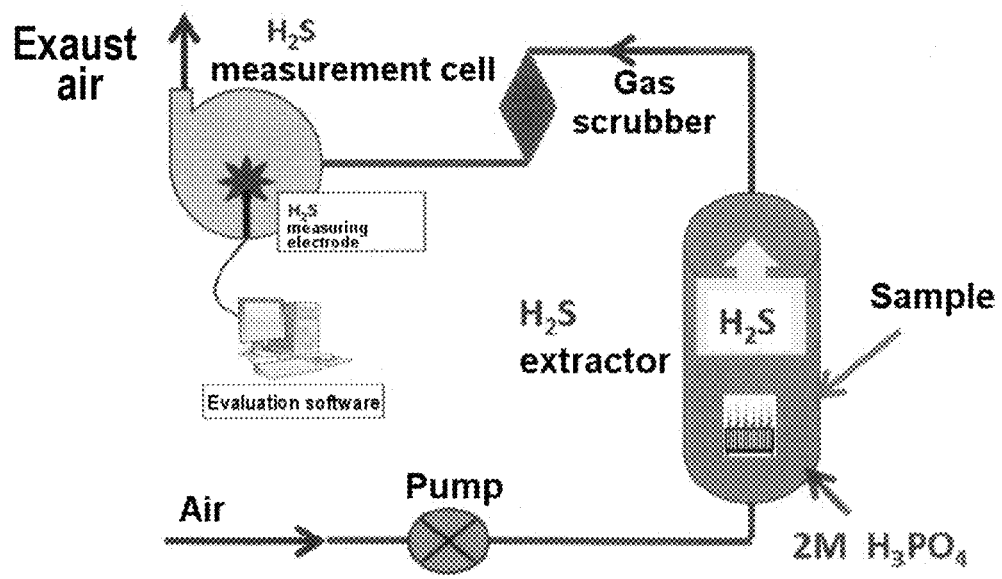

CONDENSATION PRODUCT OF 1-AMINO-2-PROPANOL AND FORMALDEHYDE AND THE USE THEREOF FOR REDUCING THE AMOUNT OF HYDROGEN SULPHIDE IN LIQUIDS AND GASES

BACKGROUND OF THE INVENTION

Field of the Invention

The present invention relates to the preparation of a condensation product of 1-amino-2-propanol and formaldehyde, the condensation product, the use thereof for reducing the amount of hydrogen sulphide in liquids and gases and also a corresponding process.

Hydrogen sulphide ($H_2S$) is an unpleasantly smelling, toxic gas which poses a great hazard to health and leads to severe corrosion phenomena in industrial plants. Lawmakers have therefore imposed strict obligations for reducing the $H_2S$ content.

Description of the Related Art

WO 02/051968 A1 discloses a process for reducing the amount of hydrogen sulphide in a liquid or a gas by treatment with an $H_2S$-scavenging product. The $H_2S$-scavenging product is obtained by reaction of i) a compound having a carbonyl group with ii) an alcohol, thiol, amide, thioamide, urea or thiourea. The product is preferably prepared by reaction of formaldehyde with amine-free alcohol or urea. An example of an amine-free alcohol is ethylene glycol. The $H_2S$-scavenging agent can optionally be used together with an amine, in particular N-(2-hydroxy ethyl) amine (ethanolamine).

WO 98/02501 discloses that bis(oxazolidine) derivatives can be used as scavenging agents for sulphur compounds. An example of a bisoxazolidine is 3,3'-methylenebis(5-methyloxazolidine), which is obtained by reaction of 1-amino-2-propanol (2-hydroxypropylamine, monoisopropanolamine, MIPA) with formaldehyde in a molar ratio of 2:3 (i.e. 1:1.5). The anhydrous condensation product Grotan® OX (3,3'-methylenebis[5-methyloxazolidine]) from Schülke & Mayr GmbH, Norderstedt, Federal Republic of Germany, displays good effectiveness in the chemical neutralization of $H_2S$.

However, it is known from various formaldehyde depot compounds used, for example, for preserving water-based products and processes that they tend to liberate formaldehyde into the gas phase and accordingly produce an unpleasant smell and also lead to instability or a neck-in effect.

According to DE 197 22 858 A1, compositions based on iodopropynyl butylcarbamate and formaldehyde depot compounds are used as preservatives. The addition of particular glycols, preferably 1,2-propylene glycol, has a positive influence on the odour of the compositions and reduces the emission of volatile materials (such as formaldehyde).

DE 102 44 442 A1 discloses a preservative which has reduced formaldehyde emission and contains a) at least one formal and b) at least one emission-reducing additive selected from among urea, urea derivatives, amino acids, guanidine and guanidine derivatives.

The preservatives according to DE 10 2004 014 447 A1 comprise a) at least N-formal, b) at least one emission-reducing additive and c) monoethylene glycol.

The product Grotan® WS (Schülke & Mayr GmbH, Norderstedt, Federal Republic of Germany) is a water-containing product which contains about 80% by weight of the formaldehyde depot compound α,α',α"-trimethyl-1,3,5-triazine-1,3,5-(2H,4H,6H)-triethanol (N,N',N"-tris(2-hydroxpropyl)hexahydrotriazine, hereinafter TTT). TTT is prepared by condensation of MIPA with formaldehyde (in a molar ratio of 1:1). The condensation product is a colourless to yellow liquid which is storage-stable and will keep for more than 36 months, but has an undesirably high viscosity, especially at low temperature. Aqueous dilutions of Grotan® WS, in contrast, are not storage-stable.

According to the teaching of EP 0 347 815 A2, alkanolamines are used for stabilizing triazine derivatives. Here, the additional presence of surfactants is said to be absolutely necessary. However, the surfactants used in the examples have poor biodegradability.

DE 27 11 106 A1 discloses a process for preparing bis(5,5'-dimethyl-1,3-oxazolidin-3-yl)methane, in which 1-amino-2-propanol is reacted with an excess of formaldehyde at elevated temperature.

DD 229 707 A1 describes a process in which alkanolamine and formaldehyde are firstly reacted with one another at a temperature in the range from 30° C. to 80° C., with it being possible to employ a stoichiometric excess of alkanolamine to increase the functionality. The products obtained after further addition of alkali metal hydroxide and reaction with alkylene oxide are used as pharmaceuticals, insecticidally or fungicidally active sub-stances or as additives for lubricating greases.

DE 26 35 389 C2 discloses preservatives and disinfectants based on condensation products of amino alcohol or amino thiol with formaldehyde. Furthermore, it is stated that an excess of formaldehyde can also be used, but this does not participate in the reaction but instead remains as free formaldehyde in the reaction mixture. The preservatives and disinfectants are suitable for aqueous paints, cooling lubricants and adhesive solutions, or for preserving cooling water circuits or water circuits in paper production.

WO 97/25126 A2 describes compositions for removing sulphides from gas streams and a corresponding regenerative process. In the process, the gas stream is brought into contact with an $H_2S$-scavenging agent, an inorganic ion and an oxidation catalyst. Examples of $H_2S$-scavenging agents are 3,3'-methylenebisoxazolidine and 1,3,5-triazine-1,3,5-(2H,4H,6H)triethanol (N,N',N"-tris(2-hydroxyethyl)hexahydrotriazine), the reaction product of monoethanolamine with formaldehyde in a molar ratio of 1:1.

WO 90/07467 A1 describes a process for selectively reducing the contents of hydrogen sulphide and organic sulphides in gaseous and/or liquid hydrocarbon streams or non-hydrocarbon streams, in which the streams are brought into contact with compositions which comprise the reaction product of (i) a lower alkanolamine with (ii) a lower aldehyde. An example of a lower alkanolamine is monoethanolamine, and an example of a lower aldehyde is formaldehyde.

WO 96/05907 A1 describes a process for reducing $H_2S$ in liquid and gaseous streams, which is characterized in that the streams are contacted with a condensation product of dialdehyde and alkanolamine. Preference is given to condensation products of glyoxal and monoethanolamine.

WO 94/08980 A1 discloses hexahydrotriazines having at least one alkoxyalkylene group and the use thereof as $H_2S$ scavengers.

US 2003/0234383 A1 proposes reacting the mixture of ethanolamine and diglycol amine with formaldehyde in order to produce an $H_2S$-scavenging agent, and in order to prevent crystalline dithiazine deposits. According to U.S. Pat. No. 8,512,449 B1, an aqueous mixture containing triazine, glycol ether and alcohol is used for scavenging sulphide.

WO2013/101361 A1 proposes using the product of the condensation of aldehyde with a secondary amine in order to scavenge $H_2S$.

DE 10 2012 203 003 A1 discloses liquid preparations for reducing free oxygen and preserving water. The preparations contain at least one N-formal and at least one dialkylhydroxylamine.

WO 2016/105341 A1 states that the use of triazine compounds for removing sulphur compounds leads to an undesirably high pH and to deposits, and instead proposes using combinations of i) an aldehyde-free compound (for example acrylate, acrylonitrile, ethyl trans-4-oxo-2-butenoate, para-benzoquinone or ortho-benzoquinone) with ii) a weak base (for example amine).

SUMMARY OF THE INVENTION

It was an object of the present invention to provide compositions which remove sulphur compounds from process streams with improved effectiveness. The compositions should be capable of storage in high concentration, without further constituents which are not absolutely necessary for the effect, e.g. antioxidants or other stabilizers, or emission-reducing additives necessarily having to be present. The compositions should additionally be able to be produced from inexpensive constituents. In addition, the compositions should preferably not lead to an undesirably high pH in aqueous dilution.

It was thus an objective of the invention to provide, in particular, a storage-stable concentrate which has a low viscosity, is stable at low temperature and is economical and which displays improved performance as $H_2S$ scavenger.

It has now surprisingly been found that this object is achieved by the use of a condensation product obtainable by reaction of 1-amino-2-propanol with formaldehyde in a molar ratio in the range from 1:2.0 to 1:3.1, with the condensation product containing less than 10% by weight of water.

The condensation product of the invention has a low viscosity, is stable at low temperature, produces no neck-in effect and is also inexpensive. It has also surprisingly been found that the condensation product of 1-amino-2-propanol and formaldehyde (in a molar ratio in the range from 1:2.0 to 1:3.1) of the invention displays a greatly improved action in the removal or reduction of $H_2S$, mercaptans, sulphides or other thiol compounds from/in water-containing or water-free gases or liquids. This improved effectiveness of the condensation product according to the invention was found both in hydrocarbon and in water and mixtures of the two. In addition, condensation products according to the invention have an advantageously low pH compared to other formaldehyde depot compounds prepared from 1-amino-2-propanol, even in aqueous dilution.

In the preparation of the condensation product, it has additionally been found, in contrast to what would have been expected from the teaching of the prior art, that condensation products of 1-amino-2-propanol and formaldehyde in a molar ratio of greater than 1:3.1 cannot be prepared. The specifically used (superstoichiometric) amount of formaldehyde is therefore crucial if the molar ratio necessary for forming the chemical compounds N,N',N''-tris(2-hydroxypropyl) hexahydrotriazine (molar ratio of 1-amino-2-propanol to formaldehyde of 1:1) and bis(5,5'-dimethyl-1,3-oxazolidin-3-yl)methane (molar ratio of 1-amino-2-propanol to formaldehyde of 1:1.5) is exceeded. It was additionally surprising that free formaldehyde was not detectable, for example by means of NMR, in condensation products according to the invention in the preparation of which formaldehyde was used in such a superstoichiometric amount.

In a first aspect, the invention provides a process for preparing a condensation product containing less than 10% by weight of water, comprising the successive steps:

Step a) of reaction of 1-amino-2-propanol is reacted with formaldehyde in a molar ratio in the range from 1:2.0 to 1:3.1 and at a temperature in the range from 50° C. to 80° C. to form a product;

Step b) of removal of water from the product obtained at the end of step a), under reduced pressure to form the condensation product.

In process as hereinbefore defined, the molar ratio of 1-amino-2-propanol to formaldehyde is preferably in the range from 1:2.2 to 1:3.1, preferably in the range from 1:2.5 to 1:3.1, more preferably in the range from 1:2.7 to 1:3.1, for example in the range from 1:2.9 to 1:3.1.

Preference is also given to the reaction of step a) being carried out at a temperature in the range from 60° C. to 70° C.

Step a) is advantageously carried out using formaldehyde in the form of paraformaldehyde or in the form of formalin solution, preferably in the form of paraformaldehyde. Typically, 1-amino-2-propanol is first charged and formaldehyde is then added.

According to the invention, the removal of water in step b) is carried out at a temperature of from 50° C. to 80° C., preferably at a temperature in the range from 60° C. to 70° C.

The removal of water in step b) is preferably carried out at a pressure in the range from $10^2$ to $10^4$ Pa (1 to 100 mbar), more preferably at a pressure in the range from $5 \times 10^2$ to $5 \times 10^3$ Pa (5 to 50 mbar), in particular at a pressure of about $10^3$ Pa (10 mbar).

In all embodiments of the invention, the condensation product preferably contains less than 8% by weight of water, more preferably less than 6% by weight of water, in particular less than 5% by weight of water, e.g. less than 4% by weight of water, or less than 3% by weight or less than 2% by weight of water, for example 1% by weight of water or less.

In a second aspect, the invention provides a condensation product containing less than 10% by weight of water, obtainable by reaction of 1-amino-2-propanol with formaldehyde in a molar ratio in the range from 1:2.0 to 1:3.1.

In a third aspect, the invention provides for the use of the condensation product as hereinbefore defined, for removing sulphur compounds from process streams.

The process stream treated according to the invention is preferably selected from liquid and gaseous process streams. Preferred process streams contain water, hydrocarbon or a mixture of water and hydrocarbon.

The sulphur compound of which amount is reduced according to the third aspect is preferably selected from among hydrogen sulphide, inorganic and organic sulphides, mercaptans and mercaptides, with the composition preferably being used for removing hydrogen sulphide from process streams.

In a fourth aspect, the invention provides a process for removing one or more sulphur compounds from a process stream, in which the process stream is brought into contact with the hereinbefore defined condensation.

In a fifth aspect, the invention provides for the use of the condensation product as hereinbefore defined, for removing one or more sulphur compounds from a process stream in order to avoid deposits.

BRIEF DESCRIPTION OF THE DRAWINGS

The invention will be described in connection with FIG. 1, illustrating schematically an analytical system for the determination of H$_2$S.

DESCRIPTION OF THE PREFERRED EMBODIMENTS

The advantages of the present invention may be derived, in particular, from the following examples. All percentages are, unless indicated otherwise, by weight.

EXAMPLES

Method of Determining the Sulphide Concentration (Based on IP 570: Determination of Hydrogen Sulphide in Mineral Oils)

Description of the Method

The various sulphur scavengers are allowed to act on the sample at various temperatures and for different times. The sample is diluted with alkyl benzene in order to get into the linear working range of the analytical system.

The sample to be analysed (including sulphur scavenger) is injected into the analytical system (shown schematically in FIG. 1).

Acid (2M H$_3$PO$_4$ in water) is added, and the analytical sample is optionally heated in the analytical system.

The hydrogen sulphide formed is quantitatively driven off by means of air in the analytical system and the hydrogen sulphide is transferred to an electrochemical measuring electrode in the analytical instrument.

The hydrogen sulphide produces a measurement signal which is proportional to the respective amount of hydrogen sulphide at the electrochemical measuring electrode.

The resulting peak area (made up of measurement signal intensity against time) is determined by means of evaluation software and converted into a content of sulphide on the basis of a calibration curve.

Example 1—Lack of Storage Stability of an Aqueous Solution of a Formaldehyde Condensation Product 1-Amino-2-propanol (187.8 g, 2.5 mol) was placed in a reaction vessel and paraformaldehyde (91% pure, 247.5 g, 7.5 mol) was added a little at a time while stirring in such a way that a temperature of 70° C. was not exceeded. After addition of ⅓ of the amount of paraformaldehyde, the exothermic reaction had ended and the further addition of paraformaldehyde was carried out at from 60 to 70° C. with heating. After addition was complete, the mixture was stirred at 70° C. for about another hour, with the paraformaldehyde dissolving completely.

A clear, yellowish solution was obtained (density at 20° C.: 1.1258 g/cm$^3$; refraction index at 20° C.: 1.4503; Hazen colour number: 29).

The stability was tested by storage at t=1 month and t=3 months at temperatures of −5° C., 25° C. and 40° C. in PE bottles (Table 1).

TABLE 1

|  | −5° C. | 25° C. | 40° C. |
| --- | --- | --- | --- |
| 1 month storage at: | | | |
| Appearance (Zero value: clear y.) | clear, y. | clear, y. | clear, orange |
| Formaldehyde which can be eliminated (%) | n.d. | 45.7 | 33.5 |
| 3 months storage at: | | | |
| Appearance | clear, light yellow | clear, dark yellow | clear, orange/red |
| Formaldehyde which can be eliminated (%) (Zero value: 50%) | n.d. | 59.3 | 59.7 | y: yellowish;
n.d. = not determined;

On storage at 40° C., significant degradation and a reduced content of formaldehyde which can be eliminated was found even after one month. After storage for three months, it could be seen that the product was ultimately not storage-stable.

The condensation product of 1-amino-2-propanol and formaldehyde (in a molar ratio of 1:3) is thus not stable in aqueous solution.

Example 2—Storage Stability of a Dewatered Formaldehyde Condensation Product

1-Amino-2-propanol (150.2 g, 2 mol) was placed in a reaction vessel and paraformaldehyde (91% pure, 198 g, 6 mol) was then added a little at a time while stirring in such a way that a temperature of 70° C. was not exceeded. After addition of ⅓ of the amount of paraformaldehyde, the exothermic reaction had ended and the further addition of paraformaldehyde was carried out at from 60 to 70° C. with heating. After the addition was complete, the mixture was stirred at 70° C. for about another hour, with the paraformaldehyde dissolving completely. The water was subsequently removed under reduced pressure [max. 70° C. at 10$^3$ Pa (10 mbar)]. A slightly yellowish clear solution was formed (density at 20° C.: 1.1259 g/ml; refraction index at 20° C.: 1.4710; Hazen colour number: 18; formaldehyde which can be eliminated: 59.6%). The stability after 1 month and 3 months of storage, was tested at −5, 25 and 40° C. in PE bottles (Table 2).

TABLE 2

|  | −5° C. | 25° C. | 40° C. |
| --- | --- | --- | --- |
| Storage for 1 month at | | | |
| Appearance | clear, s.y.* | clear, s.y. | clear, s.y.h |
| Formaldehyde which can be eliminated (%) | n.d. | 59.6 | 59.8 |
| Storage for 3 months at | | | |
| Appearance | clear, s.y. | clear, s.y. | clear, s.y. |
| Formaldehyde which can be eliminated (%) | n.d. | 59.3 | 59.7 |
| Storage for 6 months at | | | |
| Appearance | clear, s.y.* | clear, s.y.* | clear, y* |
| Density at 20° C. (g/ml) | 1.1321 | 1.1297 | 1.1283 |
| Refraction at 20° C. | 1.4738 | 1.4726 | 1.472 |
| Hazen colour number | 17 | 20 | 91 |
| Formaldehyde which can be eliminated (%) | n.d. | 59.6 | 58.6 |

TABLE 2-continued

|  | −5° C. | 25° C. | 40° C. |
|---|---|---|---|
| Storage for 12 months at |  |  |  |
| Appearance | clear, s.y. | clear, light yellow | clear, yellow |
| Density at 20° C. (g/ml) | n.d. | 1.1305 | 1.1306 |
| Refraction at 20° C. | n.d. | 1.4727 | 1.4732 |
| Hazen colour number | n.d. | 70 | 531 |
| Formaldehyde which can be eliminated (%) | n.d. | 58.2 | 57.6 |
| Degradation of formaldehyde which can be eliminated compared to the zero value | n.d. | 2.3% | 3.4% | s.y.: s.y.
n.d. = not determined

On storage at 40° C., only slight degradation and an only slightly reduced content of formaldehyde which can be eliminated was thus found even after 12 months. When dewatered, the condensation product of 1-amino-2-propanol and formaldehyde (in a molar ratio of 1:3) is thus exceptionally stable.

Example 3—Viscosities and Comparative Determination of the Reduction of Hydrogen Sulphide The following formulations were studied:
Formulation BK (Comparison):
The reaction product of ethanolamine and paraformaldehyde (91% pure) in a molar ratio of 1:1 was formed. This gave 1,3,5-triazine-1,3,5-(2H,4H,6H)triethanol. The water of reaction and the water from the paraformaldehyde remained in the product.
Formulation OX (Comparison):
The reaction product of 1-amino-2-propanol and paraformaldehyde (91% pure) in a molar ratio of 2:3 was formed. This gave 3,3'-methylenebis(5-methyloxazolidine). The water of reaction and the water from the paraformaldehyde were distilled off.
Formulation OK (Comparison):
The reaction product of 1-amino-2-propanol and paraformaldehyde (91% pure) in a molar ratio of 2:3 was formed. This gave 3,3'-methylenebis(5-methyloxazolidine). The water of reaction and the water from the paraformaldehyde were distilled off. Urea and ethylene glycol were added (the mixture contained about 4.6% by weight of urea and about 9.5% by weight of ethylene glycol).
B2 (Invention):
The dewatered reaction product of 1-amino-2-propanol and paraformaldehyde (91% pure) in a molar ratio of 1:3 was prepared as described in Example 2.

The viscosities of the formulations are shown in Table 3.

TABLE 3

|  | −10° C. | 0° C. | 10° C. | 20° C. | 40° C. |
|---|---|---|---|---|---|
| BK* | 7437 mPas | 2309 mPas | 1004 mPas | 447 mPas | 105 mPas |
| OX* | 176 mPas | 74 mPas | 38 mPas | 19 mPas | 9 mPas |
| OK* | 48392 mPas | n.d. | n.d. | 907 mPas | 170 mPas |
| B2 | 1940 mPas | 540 mPas | 220 mPas | 97 mPas | n.d. | n.d. = not determined,
*Comparison

The data in Table 3 show that the condensation product according to the invention has an advantageously low viscosity over a wide temperature range, i.e. even at a low temperature of −10° C., which is advantageous for the processability of the condensation products of the invention.

The formulations mentioned were also tested according to the method indicated above to determine how they can reduce hydrogen sulphide in various matrices (solvents or solvent mixtures). 0.10% of the respective formulation was added. The results are shown in Table 4.

TABLE 4

| Solvent | Sulphide, | T(° C.) | Reaction time | BK* | OX* | OK* | B2 |
|---|---|---|---|---|---|---|---|
|  |  |  |  | Reduction in H2S (%) | | | |
| Water | 200 ppm | 50° C. | 2 h | 20.0 | 27.0 | 21.1 | 33.5 |
| Alkylbenzene | 200 ppm | 20° C. | 2 h | 8.0 | 8.8 | 11.6 | 16.3 |
| Alkylbenzene | 200 ppm | 50° C. | 2 h | 10.1 | 10.0 | 15.4 | 24.6 |
| Alkylbenzene | 100 ppm | 50° C. | 2 h | 7.4 | 3.8 | 11.2 | 44.4 |
| Alkylbenzene (+1% of water) | 200 ppm | 50° C. | 0.5 h | 51.5 | 43.3 | 50.2 | 64.4 |

*Comparison

The data in Table 4 demonstrate that the condensation product according to the invention not only reduces the content of sulphide in water and in hydrocarbons better in comparison with 3,3'-methylenebis(5-methyloxazolidine) or with 1,3,5-triazine-1,3,5-(2H,4H,6H)triethanol, but also that this improved action requires no additives and, in addition, is even more pronounced and sets in very quickly at elevated use temperature.

Example 4—Testing of Other Molar Ratios

The procedure of Example 2 was repeated, but the molar ratio of 1-amino-2-propanol to paraformaldehyde was varied in the range from 1:2 to 1:5; 1 mol of 1-amino-2-propanol was placed in a reaction vessel in each case and different amounts of paraformaldehyde (91% pure) were then added. Solutions which can be produced stably at room temperature were tested in respect of their stability by storage at −5° C., 25° C. and 40° C. in PE bottles. The results are shown in Tables 5 and 6.

TABLE 5

|  | A | B | C*** | D*** | E*** |
|---|---|---|---|---|---|
| Molar ratio* | 1:2 | 1:2.5 | 1:3.5 | 1:4 | 1:5 |
| Appearance after dewatering (70° C.) | clear, s.y. | clear, s.y. | clear, s.y. | clear, s.y. | not dissolved |
| Appearence after cooling to 20° C. | clear, s.y. | clear, s.y. | turbid, inh., | turbid, inh. |  |
| Density, 20° C. (g/cm³) | 1.0802 | 1.1041 | n.d. | n.d. | n.d. |
| Refraction index, 20° C. | 1.4714 | 1.4723 | n.d. | n.d. | n.d. |
| Formaldehyde which can be eliminated (%) | 50.2 | 54.7 | n.d. | n.d. | n.d. |

***Comparison;
n.d.: not determined;
inh.: inhomogeneous

These examples show that condensation products of 1-amino-2-propanol and paraformaldehyde in a molar ratio of 1:2 and 1:2.5 which have been dewatered according to the invention can be prepared, while dewatered condensation products of 1-amino-2-propanol and paraformaldehyde in a molar ratio of 1:3.5, 1:4 and 1:5 cannot be prepared.

The inventive, stably preparable condensation products of 1-amino-2-propanol and paraformaldehyde in a molar ratio of 1:2 and 1:2.5 (products A and B in Table 5) were additionally examined in respect of their long-term storage stability (Table 6).

TABLE 6

Storage stability of condensation products according to the invention

| | Compound A | | |
|---|---|---|---|
| | −5° C. | 25° C. | 40° C. |
| Storage for 5 months at | | | |
| Appearance | clear, s.y. | clear, s.y. | clear, light yellow |
| Formaldehyde which can be eliminated (%) | n.d. | 49.2 | 50.2 |
| % Degradation to zero value | n.d. | 2.0 | 0.0 |
| Storage for 9 months at | | | |
| Appearance | clear, s.y. | clear, y. | clear, yellow |
| Density at 20° C. (g/ml) | n.d. | 1.0817 | 1.0820 |
| Refraction at 20° C. | n.d. | 1.4719 | 1.4712 |
| Hazen colour number | n.d. | 23 | 167 |
| Formaldehyde which can be eliminated (%) | n.d. | 50.2 | 50.1 |
| % Degradation to zero value | n.d. | 0.0 | 0.2 |

| | Compound B | | |
|---|---|---|---|
| | −5° C. | 25° C. | 40° C. |
| Storage for 5 months at | | | |
| Appearance | clear, s.y. | clear, s.y. | clear, light yellow |
| Formaldehyde which can be eliminated (%) | n.d. | 54.3 | 54.4 |
| % Degradation to zero value | n.d. | 0.7 | 0.5 |
| Storage for 9 months at | | | |
| Appearance | clear, s.y. | clear, y. | clear, yellow |
| Density at 20° C. (g/ml) | n.d. | 1.1053 | 1.1059 |
| Refraction at 20° C. | n.d. | 1.4727 | 1.4730 |
| Hazen colour number | n.d. | 29 | 232 |
| Formaldehyde which can be eliminated (%) | n.d. | 54.5 | 54.3 |
| % Degradation to zero value | n.d. | 0.4 | 0.7 | n.d. = not determined

The data in Table 6 demonstrate that the condensation products of 1-amino-2-propanol and paraformaldehyde in a molar ratio of 1:2 and 1:2.5 which have been dewatered according to the invention have good storage stability.

Example 5—Testing of Particular Molar Ratios

The procedure of Examples 2 and 3 was repeated, but the molar ratio of 1-amino-2-propanol to paraformaldehyde was varied in the narrow range from 1:3.1 to 1:3.3; 1 mol of 1-amino-2-propanol was placed in a reaction vessel in each case and different amounts of paraformaldehyde (91% pure) were then added. The results are shown in Table 7.

TABLE 7

Preparation of condensation products

|  | A | B** | C** |
|---|---|---|---|
| Molar ratio* | 1:3.1 | 1:3.2 | 1:3.3 |
| Appearance after dewatering (70° C.) | clear, s.y. | clear, s.y. | slightly opaque, s.y. |
| Appearance after cooling to 20° C. | clear, s.y. | slightly opaque, s.y. | Turbid |
| Appearance after storage at 20° C. for 7 days | clear, s.y. | Turbid | Turbid, inh. |

**Comparison

The preparation of dewatered condensation products of 1-amino-2-propanol and paraformaldehyde can thus be carried out successfully according to the invention up to a molar ratio of 1:3.1, while dewatered condensation products of 1-amino-2-propanol and paraformaldehyde in a molar ratio of 1:3.2 and 1:3.3 are not stable products.

Example 5—Examination of the pH Values of Aqueous Solutions

The inventive product as per Example 2 and formulation OX was prepared as described in Example 3. Formulation WS was prepared like formulation BK in Example 3, but from 1-amino-2-propanol (and not from ethanolamine as for formulation BK) and paraformaldehyde (91% pure) in a molar ratio of 1:1. The water of reaction and the water from the paraformaldehyde remained in the product. Formulation WS is a water-containing product containing about 80% by weight of the formaldehyde depot compound α,α',α"-trimethyl-1,3,5-triazine-1,3,5-(2H,4H,6H)triethanol (N,N',N"-tris(2-hydroxypropyl)hexahydrotriazine). The pH values of aqueous solutions of the formulations WS, OX and B2 (in each case in de-ionized water) are shown in Table 8.

TABLE 8

|  | Formulation | | |
|---|---|---|---|
| Concentration, [%] | WS* | OX* | B2 |
| 0.2 | 10.3 | 10.4 | 10.0 |
| 1.0 | 10.5 | 10.4 | 9.9 |

*Comparison

The data in Table 8 show that condensation products which have been prepared according to the invention have an advantageously lower pH than other formaldehyde depot compounds prepared from 1-amino-2-propanol, even in aqueous dilution.

The invention claimed is:

1. Process for preparing a condensation product, containing less than 10% by weight of water, comprising the successive steps:
   Step a) of reaction of 1-amino-2-propanol is reacted with formaldehyde in a molar ratio in the range from 1:2.5 to 1:3.1 and at a temperature in the range from 50° C. to 80° C. to form a product;
   Step b) of removal of water from the product obtained at the end of step a), under reduced pressure to form the condensation product.

2. Process according to claim 1, wherein the reaction in step a) is carried out at a temperature in the range from 60° C. to 70° C.

3. Process according to claim 1, wherein in step a), formaldehyde is used in the form of paraformaldehyde.

4. Process according to claim 1, wherein, in step a), 1-amino-2-propanol is initially charged and formaldehyde is added.

5. Process according to claim 1, wherein the removal of water is carried out at a temperature of from 50° C. to 80° C.

6. Process according to claim 1, wherein the removal of water is carried out at a pressure in the range from $10^2$ to $10^4$ Pa (1 to 100 mbar).

7. Process according to claim 1, wherein the condensation product contains less than 4% by weight of water.

8. Condensation product obtainable by a process for preparing a condensation product, containing less than 10% by weight of water, comprising the successive steps:
   Step a) of reaction of 1-amino-2-propanol is reacted with formaldehyde in a molar ratio in the range from 1:2.5 to 1:3.1 and at a temperature in the range from 50° C. to 80° C. to form a product; and
   Step b) of removal of water from the product obtained at the end of step a), under reduced pressure to form the condensation product.

9. A method for removing sulphur compounds from process streams, comprising providing a condensation product containing less than 10% by weight of water, according to claim 8, and applying the condensation product to the process streams to remove the sulphur compounds from process streams.

10. The method according to claim 9, wherein the process stream is selected from among liquid and gaseous process streams.

11. The method according to claim 9, wherein the process stream contains water, hydrocarbon or a mixture of water and hydrocarbon.

12. The method according to claim 9, wherein the sulphur compound is selected from among hydrogen sulphide, inorganic and organic sulphides, mercaptans and mercaptides.

13. The method according to claim 9, wherein the sulphur compound is hydrogen sulphide.

14. Method for removing one or more sulphur compounds from a process stream, wherein the process stream is brought into contact with a condensation product containing less than 10% by weight of water according to claim 8.

15. A method for removing one or more sulphur compounds from a process stream in order to avoid deposits, comprising providing a condensation containing less than 10% by weight of water according to claim 8, and applying the condensation product to the process streams to remove the, one or more sulphur compounds from the process stream, thereby avoiding deposits.

16. Process according to claim 1, wherein the reaction in step a) is carried out at a temperature in the range from 60° C. to 70° C.

17. Process according to claim 1, wherein in step a), formaldehyde is used in the form of paraformaldehyde.

18. Process according to claim 2, wherein in step a), formaldehyde is used in the form of paraformaldehyde.

19. Process according to claim 1, wherein, in step a), 1-amino-2-propanol is initially charged and formaldehyde is added.

* * * * *